(12) United States Patent
Giani et al.

(10) Patent No.: US 11,666,291 B2
(45) Date of Patent: Jun. 6, 2023

(54) APPARATUS FOR DIGITAL IMAGING IN THE HEAD REGION OF A PATIENT

(71) Applicant: DE GÖTZEN S.R.L., Varese (IT)

(72) Inventors: Claudio Giani, Varese (IT); Giuseppe Rotondo, Milan (IT); Costantino Nettis, Milan (IT); Gianfranco Venturino, Milan (IT); Gerardo Rinaldi, Milan (IT)

(73) Assignee: DE GÖTZEN S.R.L.

( * ) Notice: Subject to any disclaimer, the term of this patent is extended or adjusted under 35 U.S.C. 154(b) by 0 days.

(21) Appl. No.: 17/265,754

(22) PCT Filed: Aug. 1, 2019

(86) PCT No.: PCT/EP2019/070843
§ 371 (c)(1),
(2) Date: Feb. 3, 2021

(87) PCT Pub. No.: WO2020/025778
PCT Pub. Date: Feb. 6, 2020

(65) Prior Publication Data
US 2021/0161486 A1 Jun. 3, 2021

(30) Foreign Application Priority Data

Aug. 3, 2018 (IT) .......................... 102018000007817
Jun. 7, 2019 (EP) ...................................... 19179132

(51) Int. Cl.
*A61B 6/14* (2006.01)
*A61B 6/03* (2006.01)
(Continued)

(52) U.S. Cl.
CPC ................ *A61B 6/14* (2013.01); *A61B 6/032* (2013.01); *A61B 6/035* (2013.01); *A61B 6/06* (2013.01);
(Continued)

(58) Field of Classification Search
CPC ......... A61B 6/588; A61B 6/14; A61B 6/4476; A61B 6/4452; A61B 6/035; A61B 6/4435;
(Continued)

(56) References Cited

U.S. PATENT DOCUMENTS 10,405,815 B2 * 9/2019 Choi ..................... A61B 6/5205
2007/0030950 A1 2/2007 Sa et al.
(Continued)

FOREIGN PATENT DOCUMENTS

EP 3134001 A1 3/2017
WO 2015162101 A1 10/2015

*Primary Examiner* — Irakli Kiknadze
(74) *Attorney, Agent, or Firm* — St Onge Steward Johnston and Reens LLC

(57) ABSTRACT

An apparatus for Digital Imaging in the Head Region of a Patient includes an X-ray source and an X-ray sensor, supported on i a rotary arm supported on a structure by a motor driven translation and rotation means. The rotary arm is provided with adjustment means for varying the distance between the source and the sensor. The apparatus comprises a single sensor for both panoramic imaging and computed tomography, and has a control unit, that controls the source, the sensor, the adjustment means, and the translation and rotation means and operates the apparatus in a basic operation mode for bigger patients and in an alternative operation mode for smaller patients, in which the distance between the source and the sensor is reduced as compared to the distance used for the basic operation mode.

20 Claims, 9 Drawing Sheets

(51) Int. Cl.
  *A61B 6/10* (2006.01)
  *A61B 6/00* (2006.01)
  *A61B 6/06* (2006.01)
  *A61B 6/08* (2006.01)

(52) U.S. Cl.
  CPC ............... *A61B 6/08* (2013.01); *A61B 6/102* (2013.01); *A61B 6/4435* (2013.01); *A61B 6/4441* (2013.01); *A61B 6/4452* (2013.01); *A61B 6/4476* (2013.01); *A61B 6/542* (2013.01); *A61B 6/544* (2013.01); *A61B 6/588* (2013.01)

(58) Field of Classification Search
  CPC .. A61B 6/06; A61B 6/542; A61B 6/08; A61B 6/544; A61B 6/102; A61B 6/032; A61B 6/4441; A61B 6/589; A61B 6/461; A61B 6/54; A61B 6/107; A61B 6/58; A61B 6/0492; A61B 6/10; A61B 6/405; A61B 6/545; A61B 90/37; A61B 90/39; A61B 2090/376; A61B 2090/3937; A61B 2090/3966; A61B 2090/3979; A61B 42/00; A61B 46/00; A61B 6/4482; A61B 6/4405; A61B 6/548; A61B 6/5294; A61B 6/5282; A61B 6/5264; A61B 6/463; A61B 6/5241; A61B 5/0037; A61B 6/469; A61B 6/488; A61B 6/48; A61B 6/5205; A61B 6/52; A61B 6/466; A61B 6/0407; A61B 6/40; A61B 6/4275; A61B 6/04; A61B 6/4085; A61B 6/4225; A61B 6/501; A61B 6/485; A61B 6/487; G01T 1/2964; G01T 1/02; G01T 15/08; G01T 15/20; G06N 3/02; G06T 2210/41
  USPC ........................................................... 378/38
  See application file for complete search history.

(56) References Cited

U.S. PATENT DOCUMENTS

| | | |
|---|---|---|
| 2008/0063139 A1 | 3/2008 | Pantsar et al. |
| 2013/0182822 A1* | 7/2013 | Sakaguchi ............. A61B 6/022 378/42 |
| 2015/0030119 A1* | 1/2015 | Tamura ................ A61B 6/4007 378/62 |
| 2015/0036797 A1* | 2/2015 | Nachaliel ............. A61B 6/4435 977/939 |
| 2017/0188981 A1 | 7/2017 | Park et al. |
| 2017/0311910 A1 | 11/2017 | Inglese et al. |
| 2019/0000407 A1* | 1/2019 | Muller ................... A61B 6/547 |
| 2019/0053775 A1* | 2/2019 | Arai ....................... A61B 6/501 |
| 2019/0059842 A1* | 2/2019 | Sugihara ............. A61B 6/5282 |
| 2022/0101570 A1* | 3/2022 | Kim ....................... A61B 6/501 |

\* cited by examiner

APPARATUS FOR DIGITAL IMAGING IN THE HEAD REGION OF A PATIENT

FIELD OF THE INVENTION

The invention relates to an apparatus for digital imaging in the head region of a patient comprising:
- a source for generating X-ray radiation;
- a sensor for detecting X-ray radiation, which is generated by the source and passes through a patient;
- a rotary arm for arranging the source and the sensor thereon in such a way as to be opposed to each other, wherein the rotary arm is provided with adjustment means for varying the distance between the source and the sensor;
- a supporting structure for supporting the rotary arm, wherein motor driven translation and rotation means are interposed between the rotary arm and the supporting structure.

BACKGROUND OF THE INVENTION

US 2007/0030950 A1 discloses a combined panoramic and computed tomography (=CT) apparatus for dental imaging. The apparatus includes an X-ray source and an X-ray sensor unit provided either with a panoramic sensor part or a CT sensor part for detecting X-rays, which are generated from the X-ray source and pass through a patient. The apparatus further includes a rotary arm for arranging the X-ray source and the X-ray sensor unit thereon in such a way as to be opposed to each other. The rotary arm is held by a supporting member. Driving means are provided that allow to vary the distance between the X-ray source and the X-ray sensor unit arranged opposed to each other with respect to the rotary arm.

The known apparatus can conduct panoramic imaging and CT imaging, and provides the optimum enlargement ratio according to whether the apparatus is operated in the panoramic imaging or the CT imaging mode. The optimum enlargement ratio is achieved by varying the distance between X-ray source and the X-ray sensor unit.

The known apparatus is only optimal for adult patients having a normal size. The imaging of smaller persons particularly children, however, may require modifications.

Proceeding from this related art, the present invention seeks to provide an apparatus for digital imaging in the head region also optimized for smaller patients, in particular children.

This object is achieved by an apparatus having the features of the independent claim. Advantageous embodiments and refinements are specified in claims dependent thereon.

SUMMARY OF THE INVENTION

The apparatus comprises a single sensor for both panoramic imaging and computed tomography in the head region of the patient, and a control unit, that controls the source, the sensor, the adjustment means and the translation and rotation means. The control unit is arranged for operating the apparatus in a basic operation mode for bigger patients and in an alternative operation mode for smaller patients, in which the distance between the source and the sensor is reduced as compared to the distance used for the basic operation mode. By reducing the relative distance between the source and the sensor, the dose rate and/or the exposure time can be reduced thus diminishing the radiation risk of a child to be examined.

For the alternative operation mode, the control unit can move both source and sensor towards each other, thus allowing the enlargement ratio to be preserved.

In an alternative embodiment, the apparatus is set up for the alternative operation mode by the control unit moving only the sensor towards the source that is fixed to the rotary arm. Thus, the rotary arm need only be provided with means for moving the sensor towards the source.

In a modified embodiment, the distance for the alternative operation mode is reduced by shifting the rotation axis. The source is kept fixed with respect to the rotary arm and the control unit reduces the distance by shifting a rotation axis of the rotary arm in the direction of the sensor and by moving the sensor towards the source. This allows to keep the enlargement ratio for both operation modes unchanged.

In the modified embodiment, a special operation mode may be used for computer tomography, since for computer tomography the rotation axis may be moved on a trajectory around a virtual rotation axis that is located at the object to be imaged.

For enhancing the safety of the apparatus, the sensor is moved within a housing that is stationary with respect to the rotary arm.

The adjustment means may comprise means for positioning the sensor that are selected from the group comprising:
- a mechanism including means for a lateral motion with respect to a longitudinal axis of the rotary arm,
- a mechanism including means for a swivelling motion with respect to the rotary arm,
- a scissor mechanism for varying the distance between a base attached to the rotary arm and a support structure of the sensor,
- a linear mechanism for moving the sensor along a guiding structure in the direction of the source, and
- combinations thereof.

A mechanism enabling a lateral movement of the sensor allows to adjust the sensor to the panoramic and CT imaging mode. It may also be used to compensate for the lateral shift of the sensor if the swivelling mechanism is used for adjusting the distance between source and sensor. A mechanism for performing a swivelling motion has the additional advantage of rapid position change. The same holds for a scissor mechanism. The linear mechanism offers less speed for changing the position but is particularly stable and reliable.

The adjustment means are generally motor driven so that the operator does not have to take care for adjusting the distance between source and sensor.

The apparatus can be provided with a primary collimator that is located between the source and the patient and that is opened wider in the alternative operation mode than in the basic operation mode in order to take into account the greater beam width that is required for the alternative operation mode.

In one embodiment, the radiant intensity and thus the absorbed dose rate is reduced in the alternative operation mode by reducing the X-ray generating current and/or voltage of the source.

The radiant intensity and thus the absorbed dose rate may particularly be reduced by the square of the ratio of distance between source and sensor in the alternative operation mode to the distance between source and sensor in the basic operation mode so that the exposure time may be kept unchanged.

Alternatively or additionally the exposure time of the sensor is shorter in the alternative operation mode than in the basic operation mode.

The enlargement ratio is usually the same in the alternative operation mode and in the basic operation mode so that the medical staff is provided with images having always the usual enlargement ratio.

The basic operation mode may be an adult operation mode and the alternative operation mode may be a child operation mode, so that dose rate can be optimized for children.

In one particular embodiment, the source and/or the sensor is provided with collision detection means for detecting a possible collision with the patient and/or patient positioning means during a motion of the source and/or the sensor is provided with collision detection means for detecting a possible collision between the patient and/or patient positioning means during a motion of the sensor. The collision detection means improve the security of the apparatus. The distance between source and sensor can be reduced to a minimum, so that the maximum benefit of a reduced distance between source and sensor can be used.

The collision detection means are selected from a group comprising capacitive distance sensors, ultrasonic distance sensors, optical distance sensors, and time-of-flight optical sensors or any other suitable sensors.

The distance between source and sensor may also be adjusted depending on the output of sensor means for determining physical parameters of the patient. Thus, the distance between source and sensor can be adjusted to the individual needs of a particular patient.

BRIEF DESCRIPTION OF THE DRAWINGS

Further advantages and properties of the present invention are disclosed in the following description, in which exemplary embodiments of the present invention are explained in detail based on the drawings.

DETAILED DESCRIPTION OF THE INVENTION

Figure 1:
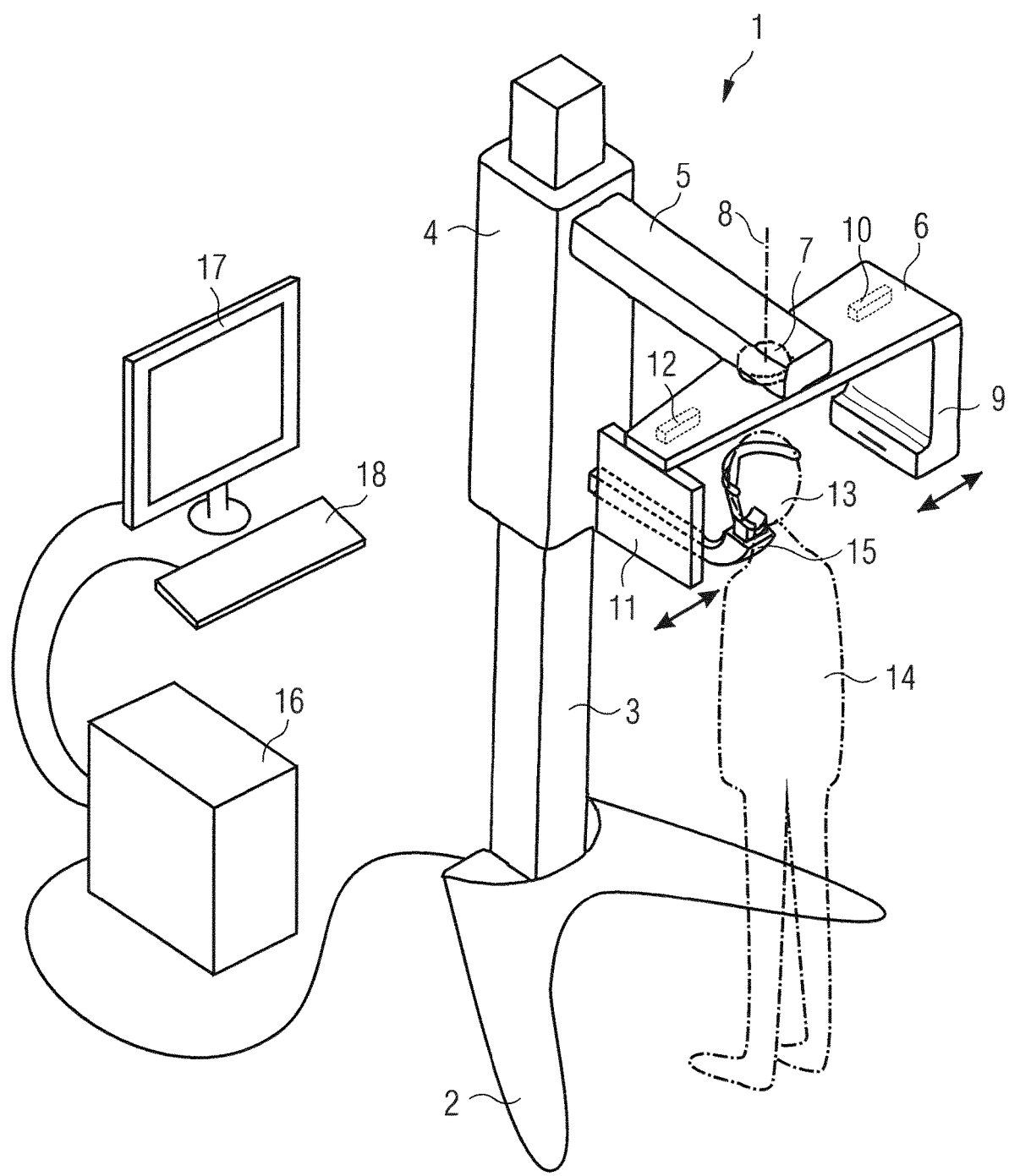
FIG. 1 shows a perspective view of an apparatus for combined panoramic and CT-imaging.

FIG. 1 shows a perspective view of a combined apparatus 1 for panoramic and CT imaging. Dental panoramic imaging is usually the imaging of a vertical image plane that follows the dental arch. Thus an image of the whole dental arch is formed. Panoramic imaging can also cover the temporomandibular joint (TMP), the sinus or the mandible or maxilla. Dental CT generally seeks to generate a three-dimensional image of a selected region of interest (ROI) along the dental arch. The ROI usually comprises a group of teeth or at least a single tooth. CT can also be used for imaging any region of the head, in particular the ear, nose and throat.

The apparatus 1 comprises a base 2 on which a pole 3 is attached that extends in a vertical direction. On the pole 3, an elevation adjustment member 4 is mounted that can slide on the pole 3 for adjusting the apparatus 1 to the tallness of a patient to be examined by the apparatus 1. A supporting arm 5 is fixed to the elevation adjustment member 4. The supporting arm 5 extends in a horizontal direction and holds on its end a rotary arm 6. Motor driven translation and rotation means 7 are interposed between the supporting arm 5 and the rotary arm 6. The translation and rotations means 7 can be used for rotating and/or translating the rotary arm 6 as required for panoramic and CT imaging. The rotary arm 6 can particularly be rotated around a rotation axis 8 and the location of the rotation axis 8 can be moved in an x-direction and a y-direction that expands a plane that is perpendicular to the rotation axis 8.

At one end of the rotary arm 6, an X-ray source 9 is located. The source 9 can be moved along the rotary arm 6 by using adjustment means 10. An X-ray sensor 11 is further provided at the other end of the rotary arm 6. The X-ray sensor 11 is a digital area sensor, usually a flat panel detector. The sensor 11 can be moved along the rotary arm 6 by using adjustment means 12.

The adjustment means 10 and 12 are preferably means for performing a translational movement along the rotary arm 6 but may also be alternative means for varying the location along the rotary arm 6. For example, the adjustment means 10 and 12 may also comprise means for performing a pivoting motion thus varying the relative distance between the source 9 and the sensor 11.

The X-ray source 9 emits X-ray radiation that passes through a head 13 of a patient 14, who is usually in a standing position during X-ray examination. During the acquisition of the X-ray images, the head 13 of the patient 14 is held by a head support 15 in a fixed position with respect to the supporting arm 5. For this purpose, the head support 15 can be attached to the elevation adjustment member 4. The head support 15 may be a simple bite, on which the patient 14 may bite during examination, but can also comprise further means for holding the head 13 in a predetermined position during the acquisition of the X-ray images. The head support 15, for instance, may also comprise means that hold the head 13 of the patient 14 in the area of the temples. The elements of the head support 15 may be fixed or movable so that the head support 15 can be adapted to the patient 14, in particular to the dimensions of the head 13.

The operation of the apparatus 1 is controlled by a control unit 16 that may be a conventional computer comprising the usual components for executing programs such as a processor, means for data transport and storage as well as various interfaces. The control unit 16 is connected to components of the apparatus 1 and executes a program for controlling these components. The control unit 16 controls for instance the motors associated with the translation and rotation means 7. The control unit 16 can also set the operational parameters of the source 9 such as the current and the voltage of the source 9, since the source 9 is generally an X-ray tube. As is well-known in the art, the current affects the radiation power of the X-ray radiation emitted by the X-ray tube, whereas the voltage affect the spectrum of the emitted X-ray radiation. The control unit 16 further performs the read-out of acquired image data from the digital area sensor 11, processes the image data and presents the resulting images on a display 17. The control unit 16 is generally also provided with some input means 18 such as a computer mouse or a keyboard that allow an operator to input commands to the control unit 16. The display 17 may also be used for entering commands. For example, the display 17 may be a touch screen on which commands can be selected by the operator from a displayed command menu. The control unit 16 is finally also arranged for controlling the adjustment means 10 and 12.

The elevation adjustment member 4 is usually operated manually. Before the acquisition of the X-ray images, the operator adjust the height of the elevation adjustment member 4 such that the patient 14 can comfortably stand in the apparatus 1.

Figure 2:
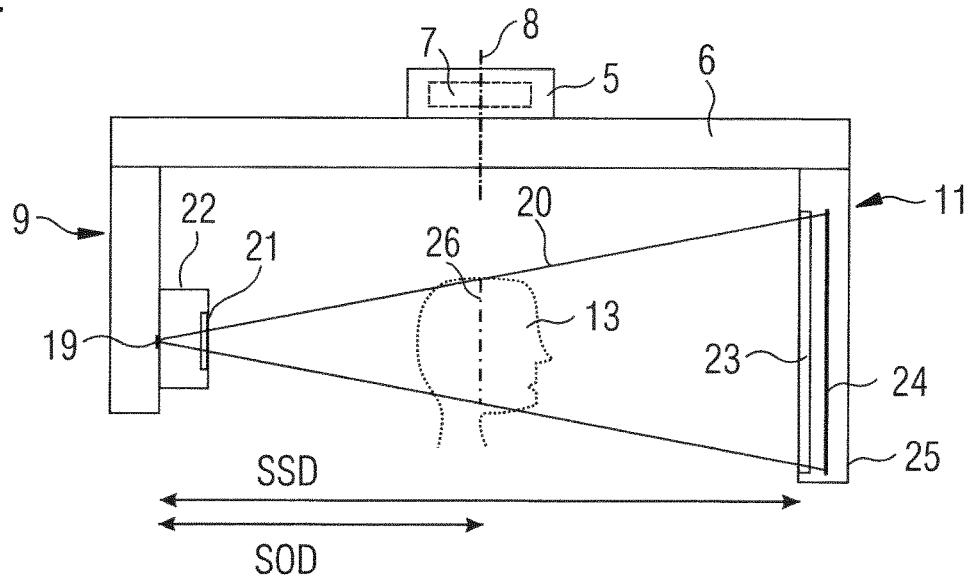
FIG. 2 is a side view demonstrating the operation of the apparatus from FIG. 1 while taking images from an adult patient.
Figure 3:
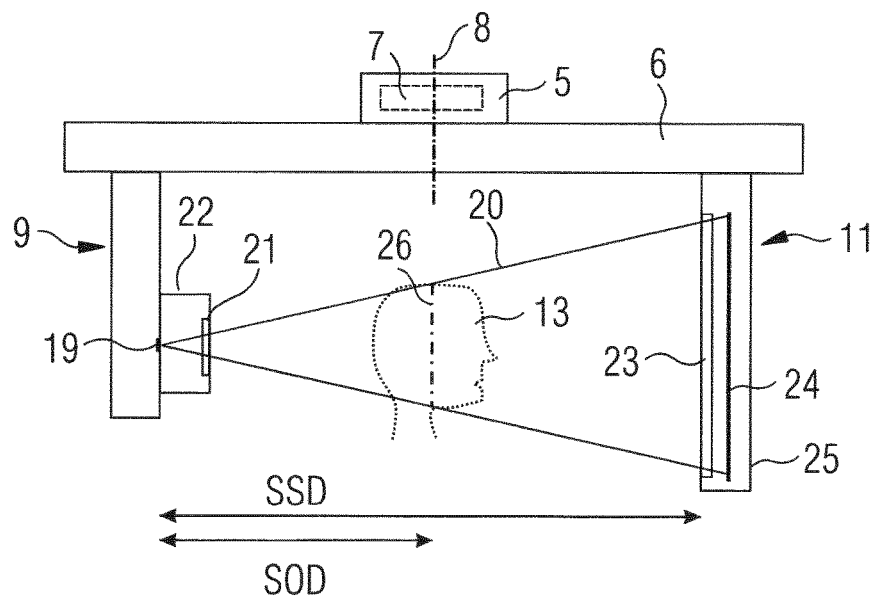
FIG. 3 is a side view demonstrating the operation of the apparatus from FIG. 1 while taking images from a child.

The apparatus 1 can now be operated in an adult operation mode and in a child operation mode that are further explained referring to FIG. 2 and FIG. 3.

FIG. 2 illustrates the basic adult operation mode, which is used if the patient 14 to be examined is an adult person. The X-ray radiation emitted from an anode 19 of the source 9 forms a beam 20. The angular extension of the beam 20 is limited by a primary collimator 21 that is located between the anode 19 of the source 9 and the patient 14 and is generally disposed within a housing 22 of the source 9. In the case of panoramic imaging, the beam 20 is a vertically aligned fan shaped beam, whereas for CT a so-called cone beam is used. Beam 20 is transmitted through the patient. Beam 20 further passes through an optional secondary collimator 23 that is located in front of a sensor plane 24 that holds the X-ray sensitive pixels of the sensor. The secondary collimator 23 can be located within a housing 25 of the sensor 11.

The pixels may be elements converting X-rays into visible light that is detected and converted into an electrical signal by an associated photosensitive element, or elements that convert impinging X-rays directly into electrical signals. These electrical signals are converted into image data by the associated sensor electronics. The image data are read out by the control unit 16.

For generating a panoramic image of the dental arch, only a selected region of the flat area sensor 11 is used, usually only a few columns of pixels, whereas for CT all pixels of sensor 11 or at least extensive areas of the sensor 11 are used.

The distance between the anode 19 of the source 9 and the sensor plane 24 of the sensor 11 is the so-called source-sensor-distance (=SSD). The distance between the anode 19 and an object 26 to be imaged within the head 13 is the so-called source-object-distance (=SOD). In the case of panoramic imaging, the object 26 is a vertical line through a point of the dental arch to be imaged by panoramic imaging. In case of dental CT the object 26 may be a vertical axis of a typically cylindrical ROI centered on a single tooth or a group of teeth, from which a three-dimensional image shall be generated by using CT. In the case of CT the object 26 coincides with the rotation axis 8. The ratio of SSD to SOD defines the enlargement ratio.

FIG. 3 illustrates the alternative child operation mode of apparatus 1. In the child operation mode, the relative distance between source 9 and sensor 11 is reduced by using the adjustment means 10 and 12. In FIG. 3, both SSD and SOD are reduced by the same factor thus preserving the enlargement ratio, al-though this is not a mandatory requirement. It is also possible to move only the source 9 or the sensor 11 or both in an asymmetric manner. Reducing the relative distance between source 9 and/or sensor 11 results in a reduced $SSD_r$ and a reduced $SOD_r$.

Figure 4:
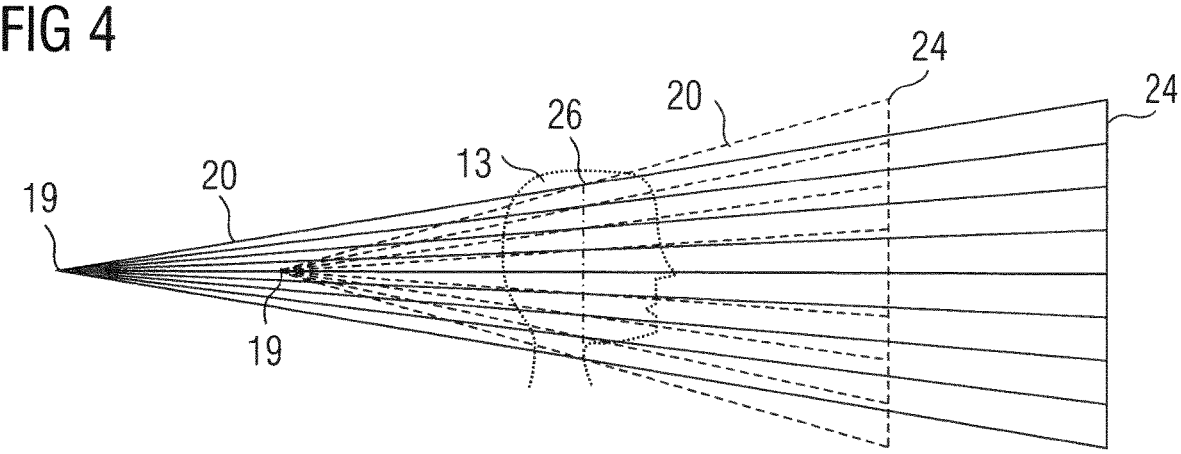
FIG. 4 is a drawing for illustrating the benefit of a particular imaging mode for children.

The benefit of the alternative child operation mode is illustrated in FIG. 4. The solid lines show the beam 20 during the adult operation mode, whereas the dashed lines depict beam 20 in the child operation mode. For the sake of simplicity, both SSD and SOD are reduced by the same factor as in FIG. 3.

For obtaining a certain signal-to-noise ratio, a certain amount of radiation energy (Joule=J) must be deposited in each pixel of the sensor 11. If the SSD is reduced, the angular extension of the sensor 11 appears to be larger as seen from the source 9. Provided that the radiant intensity (Watt/steradian) of the source 9 is kept constant, the amount of energy that is necessary for obtaining a certain signal-to-noise ratio, is obtained in less time as compared to the adult operation mode. On the other hand, if the exposure time is kept constant, the radiant intensity can be reduced. If the SOD is not reduced as shown in FIG. 4, but kept constant, a reduced radiant intensity results in a diminished absorbed dose rate (J/kg second=Gray/second) of the radiation absorbed by the head 13. Since a lower absorbed dose rate is less harmful than a higher absorbed dose rate, the reduction of the absorbed dose rate is to be preferred. If the SOD is kept constant, the reduction of radiant intensity and thus the reduction of the absorbed dose rate is proportional to $(SSD_r/SSD)^2$, wherein $SSD_r$ is the reduced SSD. If the SOD is also reduced to $SOD_r$, the reduction of the dose rate would be attenuated, because also the object 26 appears to be larger as seen from the source 9. Thus, the reduction of the dose rate would then be roughly proportional to $(SOD/SOD_r)^2 (SSD_r/SSD)^2$. If SOD and SSD are reduced by the same factor and if the radiant intensity is reduced by the square of this factor, the absorbed dose rate will remain the same.

It should be noted that a substantial reduction of the absorbed dose rate can be obtained by moving the sensor 11 as close as possible to the object 26. For example, if $SSD_r/SSD=0.85$ corresponding to a 15% decrease, the absorbed dose rate would be diminished by about 30%.

In practice the radiant intensity and thus the absorbed dose rate is diminished by reducing the current of the source 9. It should be noted that the dose rate can also be diminished by reducing the voltage of the source 9 taking into account that the optical thickness of the hard tissue in the body of a child is lower than the optical thickness of the hard tissue in the body of an adult person.

If the SOD is reduced as shown in FIG. 4, it should be noted that the primary collimator 21 must be opened more widely for the child operation mode and that the optical path of the beam rays through the patient 14 differ in adult and child operation mode as can be recognized from FIG. 4. As can further be recognized from FIG. 4, the dotted lines and the solid lines of both beams intersect the line of the object 26 at the same points. The sections of the object 26 are consequently imaged to the same pixels on the sensor plane 24. The spatial resolution of the object 26 thus may remain basically the same. It should further be noted that the enlargement ratio in the child operation mode is the same as in the child operation mode since both the source 9 and the sensor plane 24 are both shifted symmetrically with respect to the rotation axis 8.

The secondary collimator 23 can also be omitted.

In the embodiment depicted in FIG. 1, the adjustment means 10 and 12 are motor driven and operated by the control unit 16. In a simplified embodiment, however, the adjustment means 10 and 12 may also be operated manually by the operator, for instance by transferring the source 9 and/or the sensor 11 to a mark along the rotary arm 6. In this case, the apparatus may be provided with position sensors that allow the control unit 16 to check the proper positioning of the source 9 and/or sensor 11. The control unit 16 can then adapt the operational parameters of the source 9 to the selected SSD. For example, if the SSD is reduced, the radiant intensity can be reduced accordingly.

Figure 5:
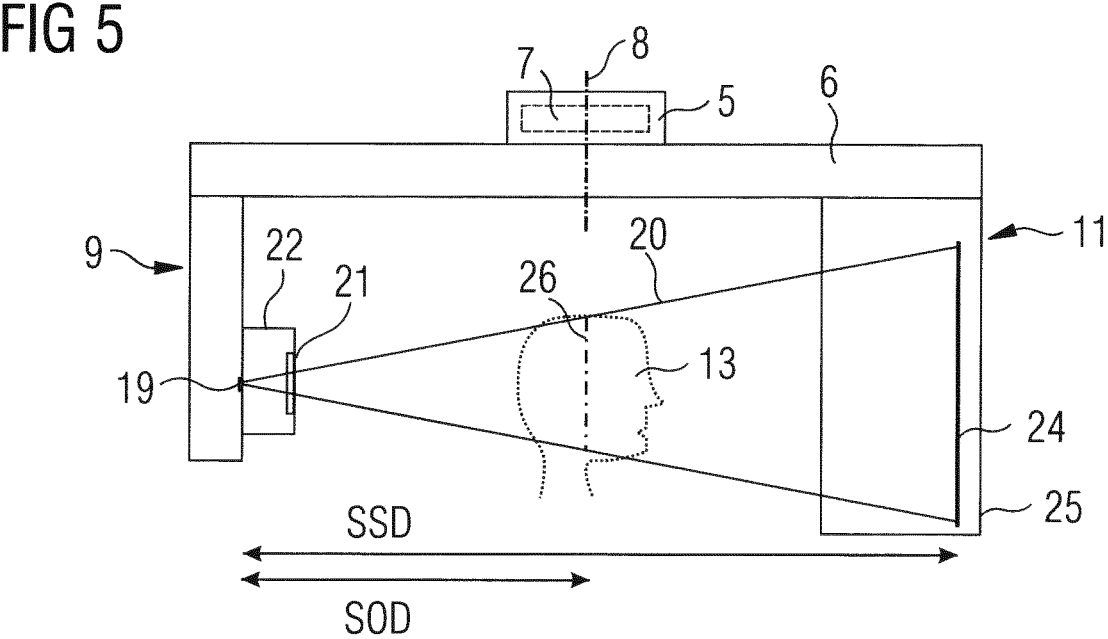
FIG. 5 is a side view of a modified apparatus operating in the adult operation mode.
Figure 6:
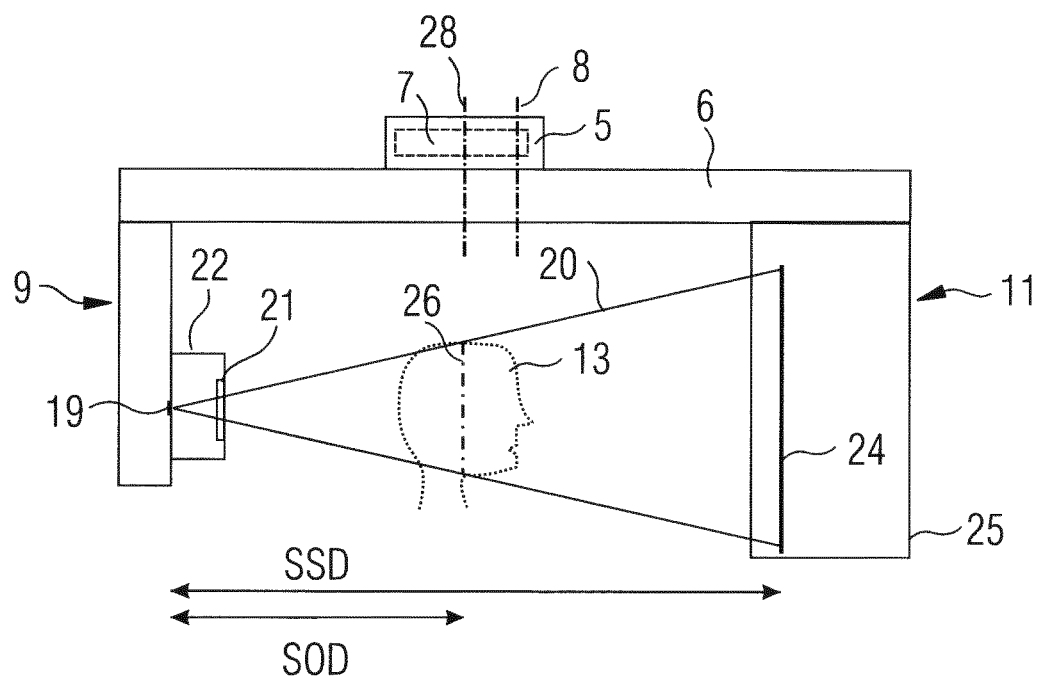
FIG. 6 is a side view of the modified apparatus from FIG. 5 operating in the child operation mode.

FIGS. 5 and 6 show a further modified embodiment. The embodiment shown in FIGS. 5 and 6 comprises an enlarged housing 27, in which the sensor 11 can perform a translatory motion in order to adjust the distance between the source 9 and the sensor 11. In the modified embodiment, the source 9 is fixed to the rotary arm 6, and the rotary arm 6 itself is moved together with the source 9 for diminishing the SOD. At the same time the sensor 11 is moved within the housing 27 towards the source 9 so that the SSD is diminished, too.

The motion of the rotary arm 6 can be performed by the translation and rotation means 7, in particular by the means that allow to shift the rotation axis 8 in the x- and y-direction. If the source 9 is shifted together with the rotary arm 6, the rotation axis 8 is no longer centered on the object 26 but transferred to some off-center position. This may affect the motion of the rotary arm 6 in the child operation mode.

Figure 7:
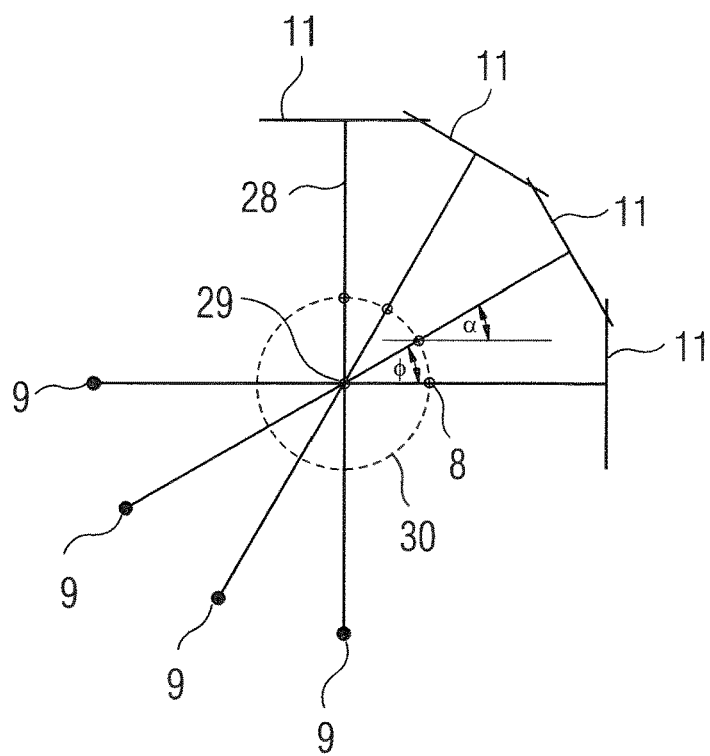
FIG. 7 illustrates the trajectory of the rotation axis when a CT image is generated from a child using the apparatus from FIG. 5.

FIG. 7 illustrates the motion of the rotary arm 6 during CT imaging in the adult and child operation mode. FIG. 7 particularly depicts various positions of the source 9, sensor 11 and a central ray 28 of the beam 20 during a CT scan of the object 26 in the child operation mode.

In the embodiments according to FIGS. 2 and 3, the rotation axis 8 is kept stationary for generating a CT image in the adult operation mode and the child operation mode, and the rotary arm 6 generally performs a rotation over 180° around the stationary rotation axis 8 so that the source 9 and the sensor 11 perform a semicircular motion around the rotation axis 8. In the child operation mode of the modified embodiment depicted in FIGS. 5 and 6, the rotary arm 6 may be moved such that the source 9 and the sensor 11 are pivoted around a virtual rotation axis 29. The motion around the virtual rotation axis 29 is achieved by moving the rotation axis 8 along a circular trajectory 30. The circular trajectory 30 is centered on the virtual rotation axis 29 and the rotation angle φ indicating the position of the rotation axis 8 on the circular trajectory 30 is in phase with the pivoting angle α of the rotation performed by the rotary arm 6 around the rotation axis 8. This particular motion along the circular trajectory 30 would preserve the enlargement ratio. It is, however, also possible to change the enlargement ratio in the child operation mode of the modified embodiment depicted in FIGS. 5 and 6 by moving the sensor plane 24 towards the rotation axis 8, by keeping the location of the rotary axis 8 unchanged and by rotating the rotary arm 6 around the rotation axis 8.

Figure 8:
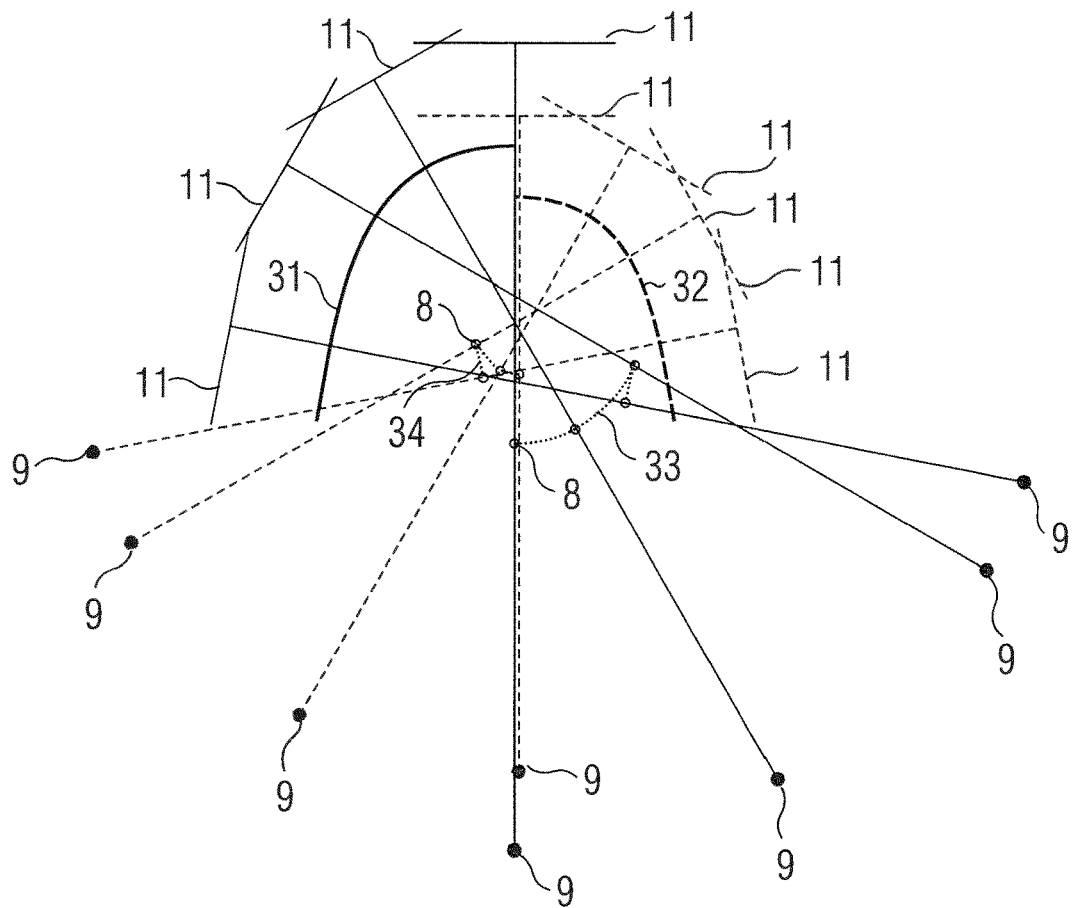
FIG. 8 illustrates the trajectory of the rotation axis when a panoramic image is generated from a child using the apparatus from FIG. 5.

FIG. 8 illustrates the motion of the rotary arm 6 during panoramic imaging. As in FIG. 7, the source 9, the sensor 11 and the central ray 28 of beam 20 is depicted in various positions during panoramic imaging on a dental arch 31 of an adult person and a dental arch 32 of a child. During panoramic imaging the rotation axis 8 is moved such that the central ray 28 of beam 20 is essential at a right angle to the respective dental arch 31 or 32. The rotation axis 8 is further moved such that the enlargement ratio with respect to the vertically aligned plane to be imaged is unchanged. If the embodiment from FIGS. 5 and 6 is used, the rotation axis 8 is moved along a trajectory 33 in the adult operation mode for imaging the dental arch 31 of an adult person. If a child is to be examined, the distance between source 9 and sensor 11 is diminished by shifting the rotation axis 8 and by moving the sensor 11 along the rotary arm 6 towards the source 9 resulting in a modified trajectory 34. This particular motion along the trajectory 34 would preserve the enlargement ratio. It is, however, also possible to change the enlargement ratio in the child operation mode of the modified embodiment depicted in FIGS. 5 and 6 by moving the sensor plane 24 towards the rotation axis 8 and by using the trajectory 33 also for the child operation mode. In this case the enlargement ratio is preferably reduced by no more than 10% or 20%.

For the sake of completeness it shall be noted that the embodiment according to FIGS. 2 and 3 comprises principally the same trajectory for both adult and child operation mode provided that the dental arches are the same or about the same.

The motion of the sensor 11 can be accomplished by various mechanisms.

Figure 9:
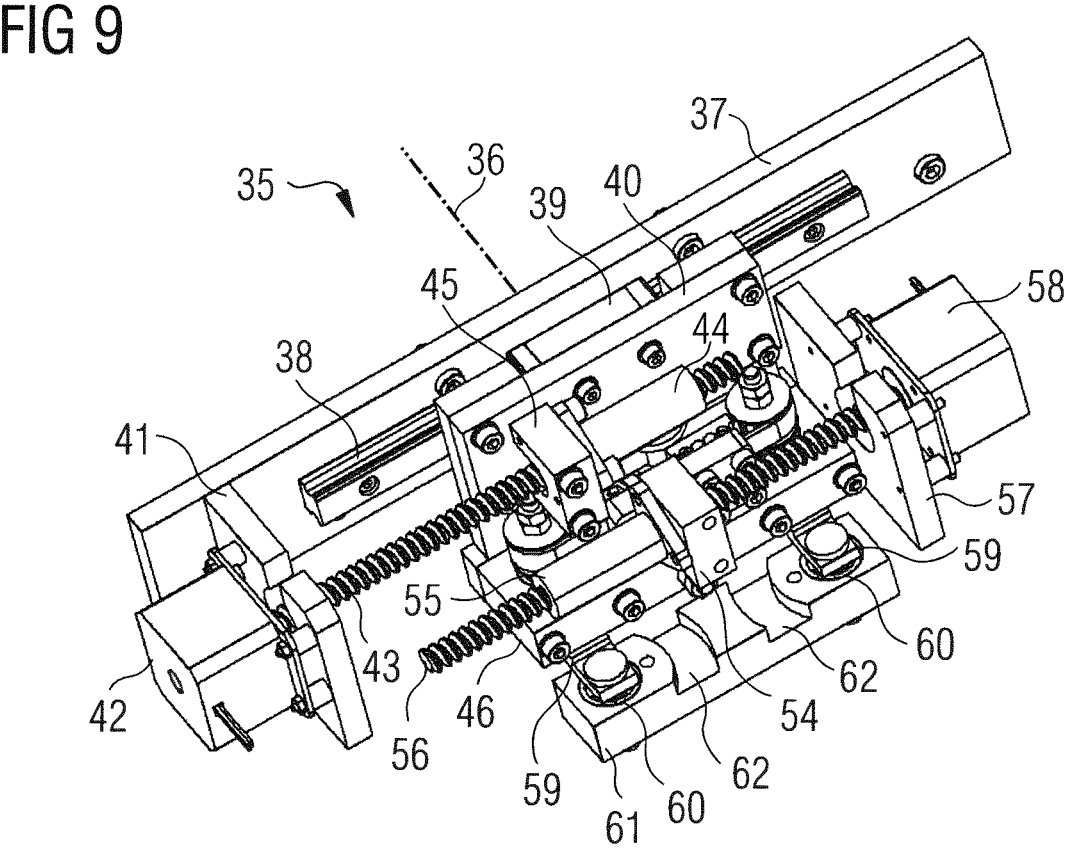
FIG. 9 shows a perspective view of a mechanism for moving the sensor.

FIG. 9 is a perspective view of a mechanism 35 for performing a roto-translation with the sensor 11 within the housing 27 of the sensor 11. The mechanism 35 is oriented at a right angle with respect to a longitudinal axis 36 of the rotary arm 6. The longitudinal axis 36 of the rotary arm 6 is usually parallel to the central ray 28 of the beam 20. A base plate 37 of the mechanism 35 is oriented at a right angle with respect to the longitudinal axis 36 of the rotary arm 6. A guiding rail 38 is affixed to the base plate 37. A guiding block 39 can slide on guiding rail 38, so that a shiftable plate 40 can be shifted along base plate 37. For controlling the motion of the shiftable plate 40, a motor plate 41 is affixed to one end of the base plate 37. The motor plate 41 holds a translation motor 42 that drives a lead screw 43 which extends along the rail 38. The lead screw 43 engages a lead screw cartridge 44 that is moved along the lead screw 43 if the lead screw 43 is turning. The lead screw cartridge 44 is attached to lead screw block 45, which is affixed to the shiftable plate 40. If the motor 42 is driving the lead screw 43, the shiftable plate 40 is thus moved along guiding rail 38.

Figure 10:
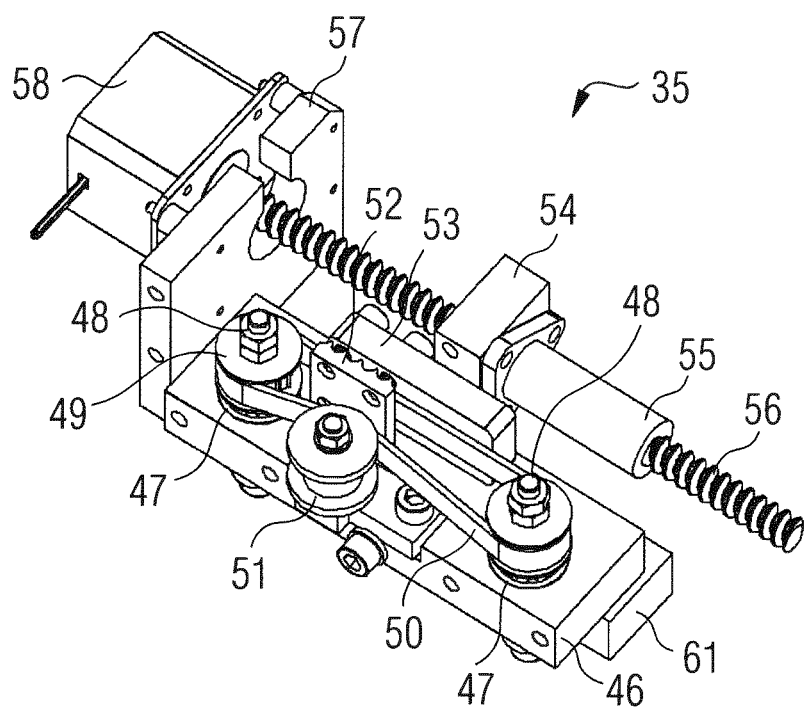
FIG. 10 is a perspective view of a part of the mechanism from FIG. 9.

The shiftable plate 40 holds an extension plate 46, which supports further parts of the mechanism 35. These parts can be recognized from FIG. 10. On opposite ends of the extension plate 46, bearings 47 are provided, each holding a gudgeon 48. On one end of each gudgeons 48, a belt pulley 49 is mounted. Both belt pulleys 49 stretch a cam belt 50 that is tensioned by a jockey pulley 51 disposed on one side of the cam belt 50 between both belt pulleys 49. On the opposite portion of the cam belt 50, a fixing plate 52 and drive plate 53 clamp the cam belt 50. A lead screw block 54 is attached to the drive plate 53. The lead screw block 54 supports a lead screw cartridge 55, that is mounted on a lead screw 56. For driving the lead screw 56, a motor plate 57 is fixed to one end of the extension plate 46. The motor plate 57 holds a swivel motor 58, that drives the lead screw 56. If the motor 58 turns the lead screw 56, the drive plate 53 and fixing plate 52 are moved together with the cam belt 50. The motion of the cam belt 50 causes a rotation of the gudgeons 48.

Figure 11:
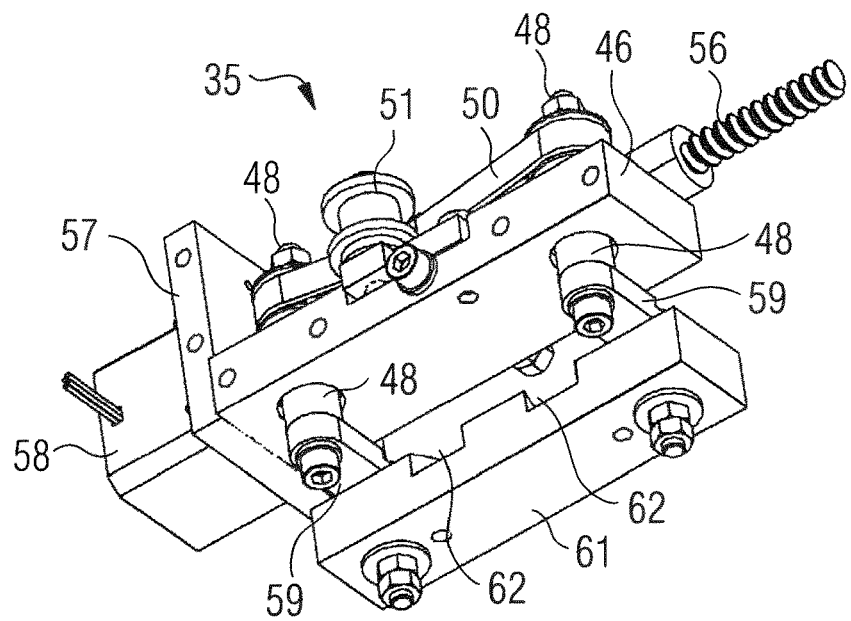
FIG. 11 is a perspective view of the part from FIG. 10 as seen from below.

As can be recognized from FIG. 11, the rotation of the gudgeons 48 results into a swiveling motion of swivel arms 59 that are mounted to the other end of the gudgeons 48 below the extension plate 46. The opposite end of the swivel arms 59 engage in bearings 60 that are held by a swivel plate 61. The swivel plate 61 finally holds the sensor 11. The swivel plate 61 is provided with channels 62 that allow the heads of the gudgeons 48 to pass over the swivel plate 61.

The mechanism 35 can be used for moving the sensor 11 in a lateral direction with respect to the longitudinal axis 36 of the rotary arm 6 in order to adjust the position of the sensor 11 for panoramic or CT imaging. The mechanism 35 can further be used to adjust the distance between source 9 and sensor 11 by pivoting the swivel arms 59 so that the swivel plate 61 is performing a motion in the direction of the longitudinal axis 36 of the rotary arm 6. The swivel arms 59 are preferably pivoted by 180° but may also be pivoted by a smaller angle. In this case, the lateral shift can be compensated by a corresponding lateral movement along the rail 38.

The main advantage of the mechanism 35 is that the sensor 11 can be moved relatively fast in the direction of the source 9, because for rotating the swivel arms 59 by 180° the lead screw cartridge 55 has to be moved only over a short distance and the distance covered the rotation of the swiveling arms 59 is twice the length of the swivel arms 59. A further advantage is that mechanism 35 also allows a lateral movement of the sensor for adjusting the position of the sensor 11 according to the requirements of panoramic and CT imaging.

Figure 12:
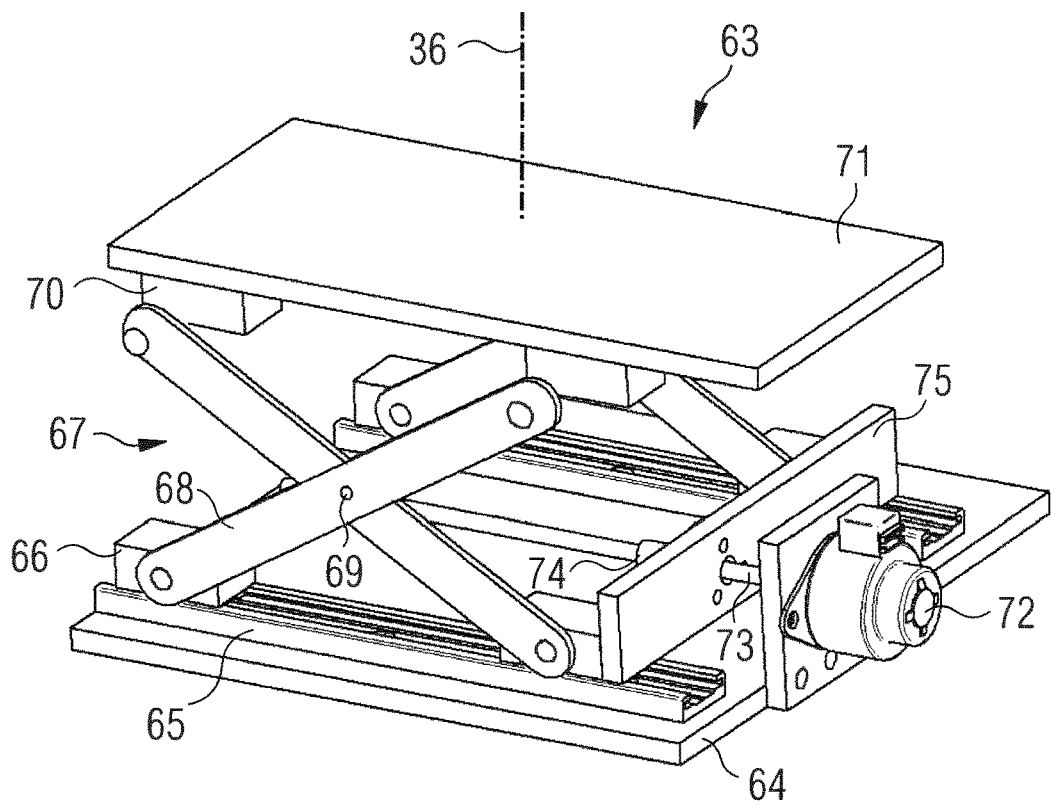
FIG. 12 is a perspective view of another mechanism for moving the sensor.

FIG. 12 depicts an alternative mechanism, where the distance between source 9 and sensor 11 is varied by using a scissor mechanism 63. The scissor mechanism 63 comprises a base 64 that is oriented at a right angle with respect to the longitudinal axis 36 of the rotary arm 6. Two parallel rails 65 are attached to the base 64. Sliding blocks 66 are mounted on the rails 65 and hold a folding support 67 comprising struts 68, whose one ends are movably attached to the sliding blocks 66. Two of the struts 68 are each connected by a central crossing bearing 69 and support with their other ends holding blocks 70 that hold a support plate 71, on which the sensor 11 can be mounted. The folding support 67 is driven by a motor 72 that is mounted on the base 64. The motor 72 drives a lead screw 73, that is engaged in a screw nut 74 affixed to a traverse 75. The traverse 75 is connected with a pair of sliding blocks 66 each mounted on opposite rails 65.

The scissor mechanism 63 also allows a rapid motion of the sensor 11, since the screw nut 74 has to move only a distance along the lead screw 73 that corresponds to half the distance the support plate 71 and thus the sensor 11 is moving towards the source 9.

Figure 13:
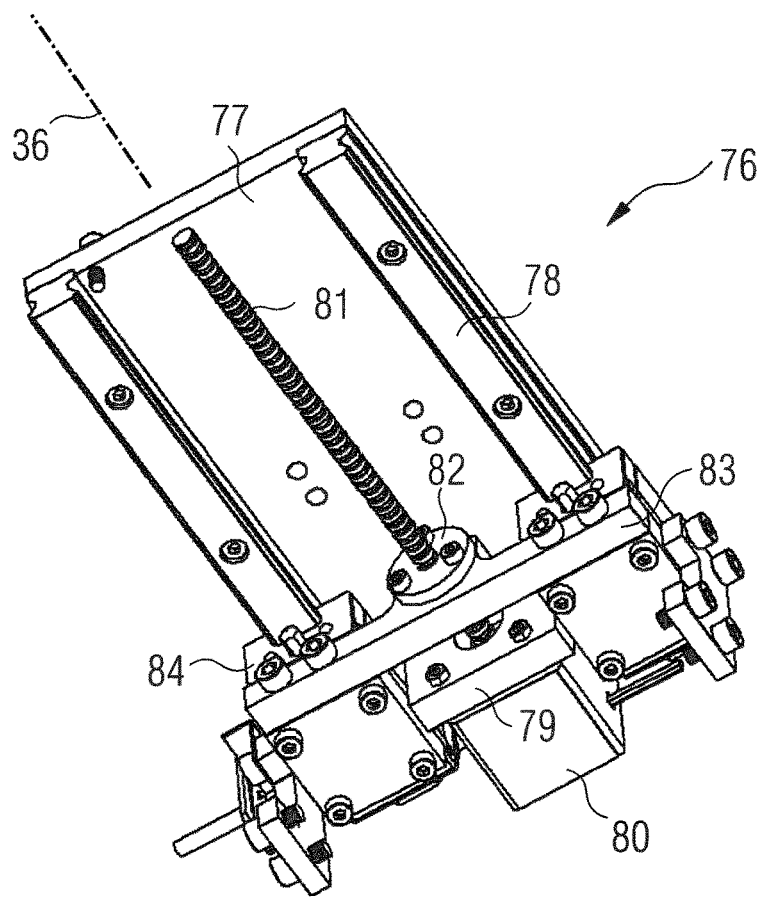
FIG. 13 is a perspective view of a further mechanism for moving the sensor as seen from below.

FIG. 13 shows a linear mechanism 76 that can also be used for varying the distance between source 9 and sensor 11. The mechanism 76 comprises a base 77 provided with rails 78. The base 77 also holds a motor support 79 that holds a motor 80 driving a lead screw 81 extending along the longitudinal axis 36 of the rotary arm 6 and engaging a screw nut 82 held by a traverse 83. The traverse 83 extends between the rails 78 and is held by sliding blocks 84 that are mounted on the rails 78. The sensor 11 is mounted on the traverse 83 such that the longitudinal axis 36 of the rotary arm 6 extends along the lead screw 81.

The particular advantage of the linear mechanism 76 is that the linear mechanism 76 is particularly stable and reliable.

It should be noted that the mechanisms described can also be combined.

It should further be noted that the child operation mode can also be used for small adult persons. It is also possible to provide several different operation modes that are applied depending on the tallness of the patient 14 to be examined. Each operation mode then uses a different distance between source 9 and sensor 11 for adapting the apparatus 1 to the particular size of the patient 14. The apparatus 1 may also be provided with sensor means for determining the size of the patient and for adjusting the distance depending on the output of the sensor means in various steps or continuously. These sensor means may be arranged for determining one or more physical parameters of the head 13 or patient 14. These parameters may be, for instance, the weight of the patient 14, the tallness of the patient 14, dimensions of the head 13, or any other suitable parameter. These parameters may also be input manually by the operator of the apparatus 1, if no sensors and not enough sensors are provided. The control unit 16 can then adapt the operational parameters of the source 9 to the selected SSD. For example, if the SSD is reduced, the radiant intensity can be reduced accordingly by reducing the current of the source.

Figure 14:
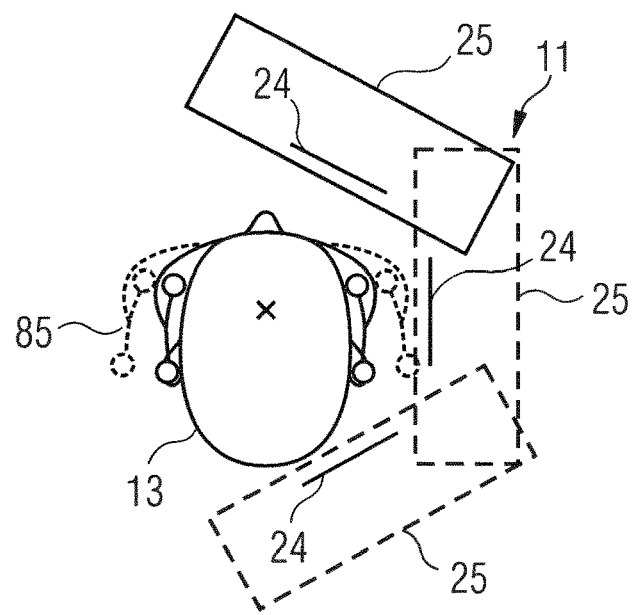
FIG. 14 illustrates collisions that might occur while operating the apparatus.

If the SSD is reduced as much as possible, collisions may occur. In particular, the housing 25 of the sensor 11 may collide with the head 13 or head support 15 as illustrated in FIG. 14, in particular since the head support 15 can be provided with a protruding temple rest 85. In FIG. 14, the temple rest 85 is depicted in a closed position, in which the temple rest 85 is in contact with the head 13, and in an open position, in which the temple rest is at a distance of the head 13. The open position is indicated by dashed lines whereas the closed position is shown in solid lines.

Figure 15:
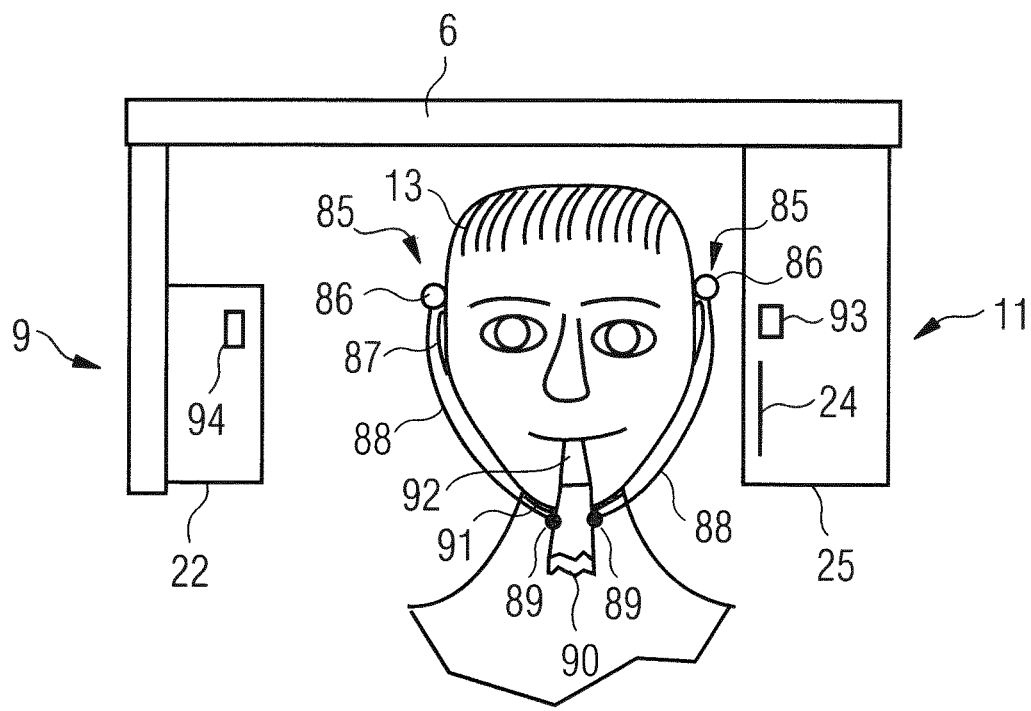
FIG. 15 shows a modified apparatus provided with collision detectors.

As can be recognized from FIG. 15, the temple rest 85 comprises two contact portions 86, that contact opposite sides of the head 13 above the ears 87. The contact portions 86 are respectively held by branches 88, whose lower ends are supported by pivot bearings 89 that are located in a base 90. The base 90 may also hold a chin rest 91 and/or bite 92, on which the patient 14 bites during examination in order to fix the position of the dentition during the scanning process.

As shown in FIG. 14, it may happen that the housing 25 of the sensor 1 collides with the temple rest 85, since the open and closed positions of the temple rest 85 are not well-defined. It may further happen that the housing 25 of the sensor 11 collides with the head 13 of the patient 14 due to an unusual shape of the head 13. The patient 14 may, for instance, have an unusual long back of the head 13 that impedes the motion of the housing 25 along a scanning trajectory.

These collisions can be avoided by direct measurements on the patient's head 13 or temple rest 85. These measurements may use mechanical measuring tools such as rulers or callipers. Also optical laser scanning techniques such as LIDAR may be used. A further alternative is the use of cameras in combination with subsequent image recognition to determine the size of the head 13 and the position of the temple rest 85. In this case, passive optical markers can be provided on the temple rest 85 in order to ensure that the image recognition safely recognizes the position of the temple rest 85. The position of the temple 85 rest can also be determined by means of passive radio markers, whose position can be detected by signals that are emitted and received by a radio-frequency transmitter. The base 90 may finally also be equipped with a position encoder that detects the angular position of the branches 88. By using one of these means or any combination of these means, the dimensions of the head 13 can be determined before the panoramic imaging or scanning for CT starts.

Despite every care in determining the dimensions of the head 13, the risk of a collision during the imaging process remains. The risk of a collision can be diminished or collisions can be avoided at all, if the sensor 11 is provided with a collision detector 93. Such a collision detector 93 can be positioned, for instance, in the housing 25 above the sensor plane 24, since the protruding part of the head 13 and the temple rest 85 are generally located above the dentition, whose image is generated by panoramic or CT imaging.

In order to avoid collisions with the source 9, the source 9 may also be associated with a collision detector 94.

In the following, various possible embodiments of the collision detectors 93 and 94 are described. For the sake of simplicity, the explanations refer only to the region around the sensor 11 and the housing 25, but the explanation are also valid for the region around the source 9 and the housing 22.

Figure 16:
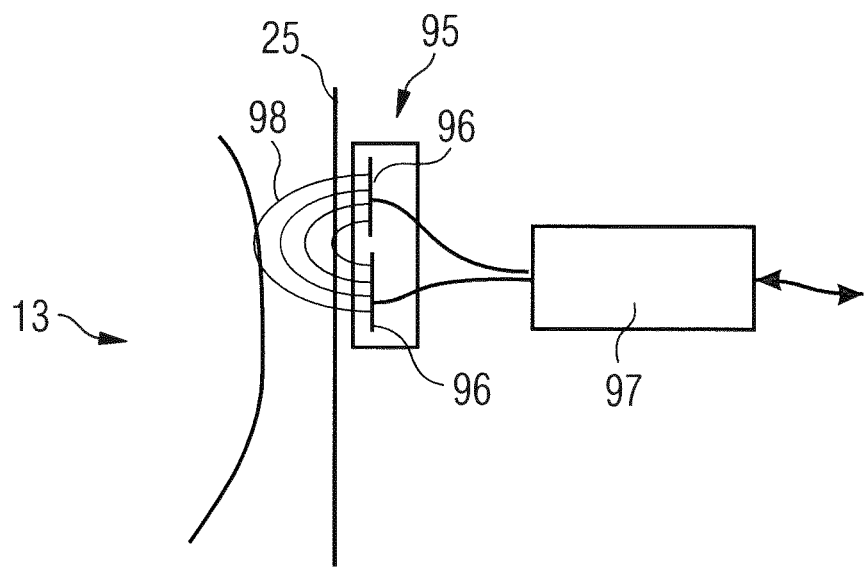
FIG. 16 illustrates the principle of operation of a capacitive collision detector.

FIG. 16 shows an embodiment, in which a capacitive distance sensor 95 is used for detecting collisions. The capacitive distance sensor 95 comprises two electrodes 96, that are connected to some sensor electronics 97, that can be read out by the control unit 16.

The electrodes 96 generate an electrical field 98 that is disturbed if an object, namely the head 13 or the temple rest 85, approaches the electrodes 96. Thus, the capacitance of the electrodes 96 changes and an imminent collision of the housing 25 with the head 13 or temple rest 85 can be detected by the sensor electronics 97 and thus by the control unit 16.

Figure 17:
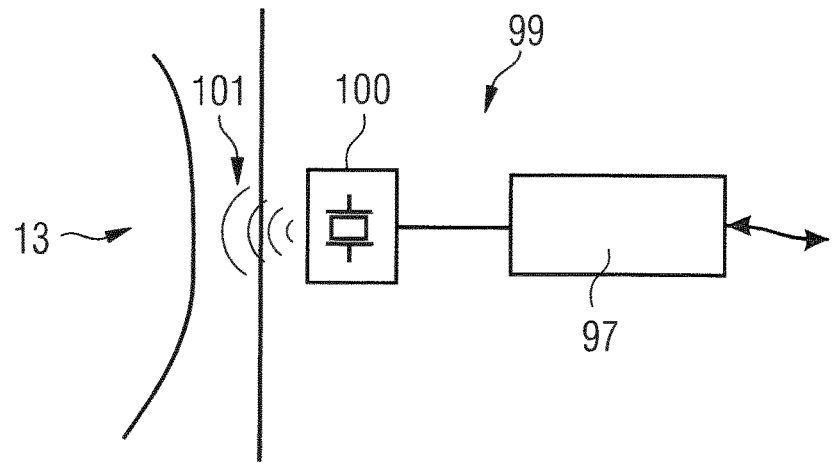
FIG. 17 illustrates the principle of operation of an ultrasonic collision detector.

FIG. 17 shows another embodiment, in which an ultrasonic distance sensor 99 is used for detecting collisions. The sensor electronics 97 of the exemplary ultrasonic sensor 99 operates an ultrasonic transceiver 100, which emits and receives an ultrasonic signal 101, that is reflected by the head 13 or the temple rest 85. The time-of-flight of the ultrasonic signal 101 is measured and used for determining the distance between the ultrasonic transceiver 100 and the head 13 or temple rest 85. The sensor electronics 97 is consequently also able to detect an imminent collision.

Figure 18:
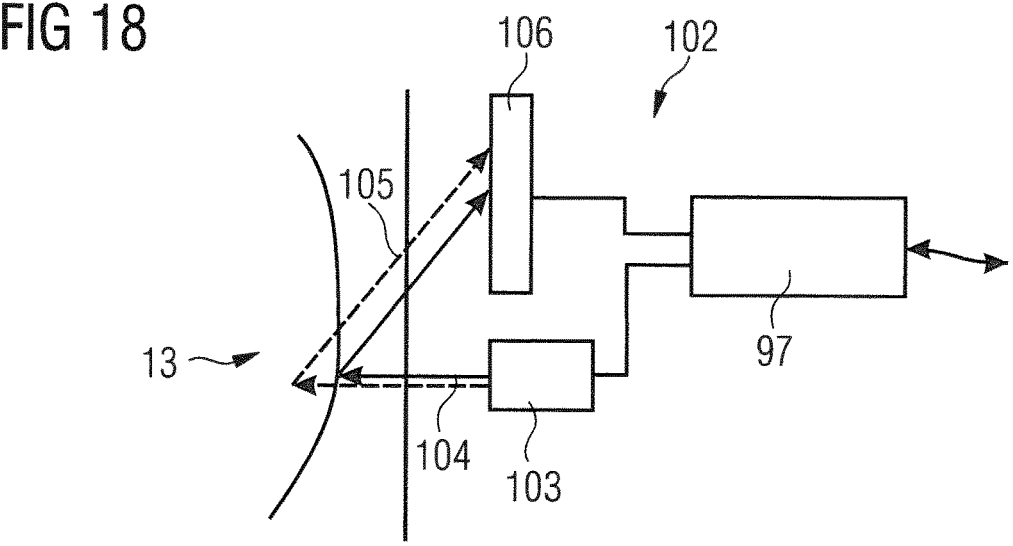
FIG. 18 illustrates the principle of operation of an optical distance sensor.

FIG. 18 shows a further embodiment, in which an optical distance sensor 102 is used for detecting collisions. The optical distance sensor 102 is based on the principle of triangulation. The optical distance sensor comprises a light source 103, for instance a laser or LED, that emits a beam 104. The beam 104 can be reflected by the head 13 or temple rest 85. Reflected light 105 impinges on a position sensitive detector 106. The information on the position, at which the reflected light hits the position sensitive detector 106, is used by the sensor electronics 97 for determining the distance between the optical distance sensor 102 and the head 13 or the temple rest 85. The sensor electronics 97 of this embodiment is consequently able to detect an imminent collision.

Figure 19:
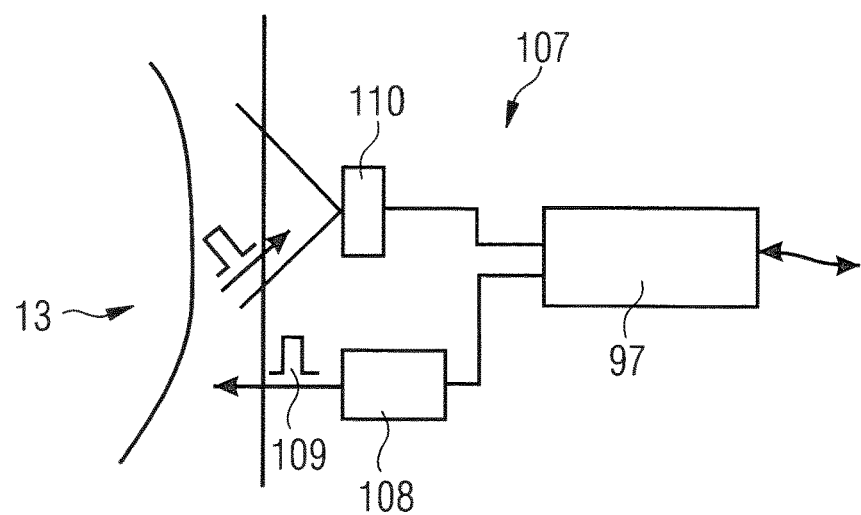
FIG. 19 illustrates the principle of a time-of-flight optical sensor.

FIG. 19 shows a fourth embodiment, in which an optical time-of-flight (=TOF) sensor 107 is used for detecting collisions. The optical TOF sensor 107 comprises a light source 108, that emits light pulses 109. The light pulses 109 are reflected at the head 13 or temple rest 85 and received by a light detector 110. The time of flight is measured by the sensor electronics 97 and based on the measurement, the distance, that the light pulse 109 has travelled between the light source 108 and the light detector 110, can be determined.

It is an advantage of the optical systems that the results are independent from the ambient conditions, such as temperature or air humidity.

The examples for collision detectors shown in FIGS. 16 to 19 shall not be understood as being limiting. Any other distance sensor can be considered, for instance also visual systems that process images from camera data for recognizing the risk of a collision with an object in the field-of-view of the camera.

Finally, it should also be noted that the invention has been described here with regard to a dental imaging apparatus. The invention, however, can generally also be used for apparatuses that are used for imaging any region in the head 13 of the patient 14, for instance for an apparatus that is used for imaging the mandible or maxilla, the temporomandibular joint or the sinus by panoramic imaging and/or that is used for imaging any other region of the head 13 by CT, in particular regions around the ear, nose and throat of the patient 14.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, components or groups described in conjunction with a particular aspect, embodiment or example of the invention are to be understood to be applicable to any other aspect, embodiment or example described herein unless incompatible therewith.

The invention claimed is:

1. An apparatus for digital imaging in the head region of a patient comprising:
   a source for generating X-ray radiation;
   a sensor for detecting X-ray radiation, which is generated by the source and passes through the patient, wherein the sensor is a single sensor for both panoramic imaging and computed tomography in the head region of the patient;
   a rotary arm, wherein the source is positioned in a location at one end of the rotary arm, and the sensor is movably positioned at another end of the rotary arm opposite the source by an adjustment device configured to move the sensor towards the source, thereby varying the distance between the source and the sensor;
   a supporting structure for supporting the rotary arm, wherein motor driven translation and rotation means are interposed between the rotary arm and the supporting structure; and
   a control unit that controls the source, the sensor, the adjustment device, and the translation and rotation means and that is configured to operate the apparatus in a basic operation mode for a first set of patients and in an alternative operation mode for a second set of patients, wherein, in the alternative operation mode, the control unit is configured to operate the adjustment device to move only the sensor towards the source, to thereby reduce the distance between the source and the sensor as compared to the distance used for the basic operation mode by moving only the sensor towards the source and the control unit is further configured to reduce a radiant intensity of X-ray radiation generated by the source by reducing an X ray generating current and/or a voltage of the source to thereby reduce X-ray radiation exposure of the patient.

2. The apparatus according to claim 1, wherein the control unit additionally shifts a rotation axis of the rotary arm.

3. The apparatus according to claim 2, wherein, for computer tomography, the rotation axis is moved on a trajectory around a virtual rotation axis that is located at the object to be imaged.

4. The apparatus according to claim 1, wherein the sensor is moved within a housing that is stationary with respect to the rotary arm.

5. The apparatus according to claim 1, wherein the adjustment device is selected from the group consisting of:
a mechanism configured for a lateral motion with respect to a longitudinal axis of the rotary arm,
a mechanism configured for a swiveling motion with respect to the rotary arm,
a scissor mechanism for varying the distance between a base attached to the rotary arm and a support structure of the sensor,
a linear mechanism for moving the sensor along a guiding structure in the direction of the source, and
combinations thereof.

6. The apparatus according to claim 1, wherein the adjustment device is motor driven.

7. The apparatus according to claim 1, wherein the apparatus is provided with a primary collimator that is located between the source and the patient and that is opened wider in the alternative operation mode than in the basic operation mode.

8. The apparatus according to claim 1, wherein an exposure time of the sensor is reduced in the alternative operation mode as compared to the basic operation mode.

9. The apparatus according to claim 1, wherein the radiant intensity of the source is reduced by the square of the ratio of the distance between source and sensor in the alternative operation mode to the distance between source and sensor in the basic operation mode.

10. The apparatus according to claim 1, wherein an enlargement ratio of the panoramic imaging and/or computed tomography in the head region of the patient is the same in the alternative operation mode and in the basic operation mode.

11. The apparatus according to claim 1, wherein the first set of patients are adult patients and the second set of patients are child patients.

12. The apparatus according to claim 1, wherein the distance between source and sensor is adjusted depending on the output of sensor means for determining physical parameters of the patient.

13. The apparatus according to claim 1, wherein the source is provided with collision detection means for detecting a possible collision of the source with the patient and/or patient positioning means during a motion of the source and/or that the sensor is provided with collision detection means for detecting a possible collision of the sensor with the patient and/or patient positioning means during a motion of the sensor.

14. The apparatus according to claim 13, wherein the collision detection means are selected from a group comprising capacitive distance sensors, ultrasonic distance sensors, optical distance sensors, and time-of-flight optical sensors.

15. An apparatus for digital imaging in the head region of a patient comprising:
a source for generating X-ray radiation;
a sensor for detecting X-ray radiation, which is generated by the source and passes through the patient, wherein the sensor is a single sensor for both panoramic imaging and computed tomography in the head region of the patient;
a rotary arm, wherein the source is positioned at a location at one end of the rotary arm, and the sensor is movably positioned at another end of the rotary arm opposite the source;
a supporting structure for supporting the rotary arm, wherein motor driven translation and rotation means are interposed between the rotary arm and the supporting structure;
the translation and rotation means being configured to shift the rotary arm in the direction of the sensor, whereby the source is positioned nearer to the patient;
an adjustment device configured to move the sensor towards the source;
a control unit that controls the source, the sensor, the adjustment device, and the translation and rotation means, and that is configured to operate the apparatus in a basic operation mode for a first set of patients and in an alternative operation mode for a second set of patients;
wherein, in the alternative operation mode, the control unit is configured to operate the translation and rotation means to shift the rotary arm in the direction of the sensor whereby the source is positioned nearer to the patient and to operate the adjustment device to move only the sensor nearer to the patient, and the control unit is further configured to reduce a radiant intensity of X-ray radiation generated by the source by reducing an X-ray generating current and/or a voltage of the source to thereby reduce X-ray radiation exposure absorbed by the patient.

16. The apparatus according to claim 15, wherein the adjustment device is selected from the group consisting of:
a mechanism configured for a lateral motion with respect to a longitudinal axis of the rotary arm,
a mechanism configured for a swiveling motion with respect to the rotary arm,
a scissor mechanism for varying the distance between a base attached to the rotary arm and a support structure of the sensor,
a linear mechanism for moving the sensor along a guiding structure in the direction of the source, and
combinations thereof.

17. The apparatus according to claim 15, wherein the first set of patients are adult patients and the second set of patients are child patients.

18. An apparatus for digital imaging in the head region of a patient comprising:
a source for generating X-ray radiation;
a sensor for detecting X-ray radiation, which is generated by the source and passes through the patient, wherein the sensor is a single sensor for both panoramic imaging and computed tomography in the head region of the patient;
a rotary arm, wherein the source is positioned at a location at one end of the rotary arm, and the sensor is movably positioned at another end of the rotary arm opposite the source;
a supporting structure for supporting the rotary arm, wherein motor driven translation and rotation means are interposed between the rotary arm and the supporting structure;

the translation and rotation means being configured to shift a rotation axis of the rotary arm, and to shift the rotary arm in the direction of the sensor, whereby the source is positioned nearer to the patient, and to shift the rotary arm in the direction of the source, whereby the source is positioned further from the patient;

an adjustment device configured to move the sensor towards and away from the source;

a control unit that controls the source, the sensor, the adjustment device, and the translation and rotation means, and that is configured to operate the apparatus in a basic operation mode for a first set of patients and in an alternative operation mode for a second set of patients;

wherein, in the basic operation mode, the control unit is configured to operate the translation and rotation means to shift the rotary arm in the direction of the source, whereby the source is positioned further from the patient, and to operate the adjustment device to move the sensor away from the patient;

wherein, in the alternative operation mode, the control unit is configured to operate the translation and rotation means to shift the rotary arm in the direction of the sensor, whereby the source is positioned nearer to the patient, and to operate the adjustment device to move only the sensor nearer to the patient, and the control unit is further configured to reduce a radiant intensity of X-ray radiation generated by the source by reducing an X-ray generating current and/or a voltage of the source to thereby reduce X-ray radiation exposure absorbed by the patient.

19. The apparatus according to claim 18, wherein the adjustment device is selected from the group consisting of:
a mechanism configured for a lateral motion with respect to a longitudinal axis of the rotary arm,
a mechanism configured for a swiveling motion with respect to the rotary arm,
a scissor mechanism for varying the distance between a base attached to the rotary arm and a support structure of the sensor,
a linear mechanism for moving the sensor along a guiding structure in the direction of the source, and
combinations thereof.

20. The apparatus according to claim 18, wherein the first set of patients are adult patients and the second set of patients are child patients.

* * * * *